(12) United States Patent
Siedenburg

(10) Patent No.: US 9,091,764 B2
(45) Date of Patent: Jul. 28, 2015

(54) LIQUID MIXTURE USED TO TEST AND VALIDATE TEST DEVICES

(71) Applicant: Smiths Heimann GmbH, Wiesbaden (DE)

(72) Inventor: Uwe Siedenburg, Essenheim (DE)

(73) Assignee: Smiths Heimann GmbH, Wiesbaden (DE)

( * ) Notice: Subject to any disclaimer, the term of this patent is extended or adjusted under 35 U.S.C. 154(b) by 0 days.

(21) Appl. No.: 14/187,749

(22) Filed: Feb. 24, 2014

(65) Prior Publication Data

US 2014/0166935 A1    Jun. 19, 2014

Related U.S. Application Data

(63) Continuation of application No. PCT/EP2012/065950, filed on Aug. 15, 2012.

(30) Foreign Application Priority Data

Aug. 22, 2011 (DE) .................. 10 2011 081 328
Nov. 10, 2011 (DE) .................. 10 2011 118 107

(51) Int. Cl.
*G01T 7/00* (2006.01)
*G01V 5/00* (2006.01)
*G01N 23/02* (2006.01)
*G01N 33/22* (2006.01)

(52) U.S. Cl.
CPC .............. *G01T 7/005* (2013.01); *G01N 23/02* (2013.01); *G01N 33/227* (2013.01); *G01V 5/0016* (2013.01)

(58) Field of Classification Search
CPC .................................................. G01N 33/22
USPC ................... 436/8, 57, 131, 18; 422/68.1
See application file for complete search history.

(56) References Cited

U.S. PATENT DOCUMENTS

| 2,495,277 | A |  | 1/1950 | Navikas |
|---|---|---|---|---|
| 5,958,299 | A |  | 9/1999 | Kury et al. |
| 6,839,406 | B2 |  | 1/2005 | Ries et al. |
| 7,583,221 | B2 |  | 9/2009 | Detlefsen et al. |
| 8,563,316 | B2 | * | 10/2013 | Duffy et al. ........................ 436/8 |
| 2006/0166368 | A1 | * | 7/2006 | Berkelman .................... 436/86 |
| 2009/0194744 | A1 | * | 8/2009 | Adebimpe ................. 252/408.1 |
| 2011/0195397 | A1 | * | 8/2011 | Selinfreund et al. ........... 435/6.1 |

FOREIGN PATENT DOCUMENTS

| DE | 195 54 662 A1 | 6/2001 |
|---|---|---|
| DE | 101 25 531 A1 | 11/2002 |
| DE | 10 2005 016 106 A1 | 10/2006 |
| DE | 10 2011 081 328 A1 | 2/2013 |
| GB | 347144 | 10/1929 |
| WO | WO 2005/094768 A1 | 10/2005 |
| WO | WO 2009/136677 A1 | 11/2009 |

OTHER PUBLICATIONS

Sorby et al., "Dielectric Constants of Complex Pharmaceutical Solvent Systems I," J. of Pharma. Sci., vol. 52, No. 12, pp. 1149-1153 (Dec. 1, 1963).

Cox et al., "A Continuous-Flow, Rapid-Mixing, Photolabelling Technique Applied to the Acetylcholine Receptor," Analytical Biochemistry, vol. 136, No. 2, pp. 476-486 (Feb. 1, 1984).

Le Roux et al., "Preserving the Neurovascular Supply in the Hall-Findlay Superomedial Pedicle Breast Reduction: An Anatomical Study," J. of Plastic, Reconstructive & Aesthetic Surgery, vol. 63, pp. 655-662 (2010).

Herzen et al., "Quantitative Phase-Contrast Tomography of a Liquid Phantom Using a Conventional X-Ray Tube Source," Optics Express, Optical Soc. of Am., vol. 17, No. 12, pp. 10010-10018 (2009).

* cited by examiner

*Primary Examiner* — Jill Warden
*Assistant Examiner* — Julie Tavares
(74) *Attorney, Agent, or Firm* — Muncy, Geissler, Olds & Lowe, P.C.

(57) ABSTRACT

A liquid mixture used to test and validate test devices for inspecting objects or persons is provided. The mixture containing glycerol and consisting of a mixture of glycerol, ethanoic acid and water.

5 Claims, No Drawings

LIQUID MIXTURE USED TO TEST AND VALIDATE TEST DEVICES

This nonprovisional application is a continuation of International Application No. PCT/EP2012/065950, which was filed on Aug. 15, 2012, and which claims priority to German Patent Application No. 10 2011 081 328.4, which was filed in Germany on Aug. 22, 2011 and German Patent Application No. 10 2011 118 107.9, which was filed in Germany on Nov. 10, 2011, and which are all herein incorporated by reference.

BACKGROUND OF THE INVENTION

Description of the Background Art

German patent application DE 10 2011 081 328, which is incorporated herein by reference, describes the use of inspection systems, in which the persons or objects to be inspected are x-rayed or irradiated in screening devices by electromagnetic rays, for inspecting persons and objects, such as luggage, for hazardous materials such as blasting materials or explosives. As is generally known, such inspection systems are used at airports for inspecting passengers and luggage.

The inspection systems according to a known embodiment contain screening devices in which the objects to be inspected, for example, luggage, are x-rayed or irradiated by x-rays and the transmitted or scattered x-rays are detected and analyzed. See DE 10125531 and DE 19954662-A, which corresponds to U.S. Pat. No. 6,839,406, and which are incorporated herein by reference.

Screening devices are known for inspecting persons, in which the persons to be inspected are irradiated with electromagnetic mm waves and the scattered mm waves are analyzed to obtain an image (DE 102005016106-A, which corresponds to U.S. Pat. No. 7,583,221 (B2), and which is incorporated herein by reference).

The screening devices must be tested and validated before being placed into operation. This typically occurs with real hazardous materials, therefore the explosives to be detected. The use of explosives is regulated by law, and moreover they are difficult to handle.

U.S. Pat. No. 5,958,299 discloses an explosive simulation mixture, which contains non-explosive components, whereby the components are selected so that the mixture has a physical form, density, x-ray transmission, and an effective atomic number that corresponds to a selected explosive mixture. An x-ray screening device can be tested for the detection of the specific explosive with use of the simulation mixture instead of a real explosive. Solid, plastic, and gel-like compositions, which are made up of different components, are described as simulation mixtures.

Inspection systems are increasingly required to detect liquid explosives and so-called "home-made explosives" as well. The object of the invention therefore is to provide such a mixture that simulates blasting materials or explosives and is not explosive, non-critical in regard to handling, and economic to produce, and behaves like the real hazardous material in a screening device for inspecting objects or persons.

In DE 10 2011 081 328.4, a mixture of glycerol, sodium hydroxide (NaOH), and water is used as the simulation mixture, whereby glycerol and sodium hydroxide are present in a weight ratio of glycerol/sodium hydroxide between 6.5 and 3.8.

SUMMARY OF THE INVENTION

According to an embodiment of the invention, a liquid mixture which has a mixture of glycerol, acetic acid ($CH_3COOH$), and water is used for simulating explosive liquids. The amount of glycerol can be 29.5% by weight to 45.5% by weight, particularly about 37.5% by weight. The amount of acetic acid ($CH_3COOH$) is preferably 7.625% by weight to 23.625% by weight, particularly about 15.625% by weight. The particular amounts are brought to 100% by weight with water, whereby the amount of water is preferably between 41.85% by weight and 51.85% by weight, particularly about 46.875% by weight. The amount of acetic acid can be added, for example, as 25% vinegar essence. To obtain 15.625% acetic acid in the mixture, then 62.5% by weight of the 25% vinegar essence is added.

DETAILED DESCRIPTION

A preferred mixture has an amount of glycerol of 37.5% by weight, an amount of 15.625% by weight of acetic acid ($CH_3COOH$), and 46.875% by weight of water.

For testing and validating, the liquid simulation mixture according to an embodiment of the invention is placed in an object to be inspected or on a person. The simulation mixture has glycerol, acetic acid, and water.

The previously described basic formulation can be diluted or thickened with retention of the ratios between glycerol and acetic acid by more or less water, whereby the total mixture remains liquid. Simulation mixtures for simulating various liquid hazardous materials can be produced by the different amounts of water.

The objects to be inspected, particularly luggage, are x-rayed or irradiated with electromagnetic rays in the screening devices. The transmitted or scattered rays are detected and analyzed.

A preferred use of a mixture according to the invention is the testing and validating of x-ray screening devices for inspecting persons or objects, particularly luggage.

Likewise, the simulation mixture according to the invention can be used to test and validate screening devices in which electromagnetic mm waves are used to inspect persons or objects.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A liquid mixture for testing and validating screening devices for inspecting objects or people, the mixture consisting essentially of glycerol, acetic acid, and water,
    wherein the mixture is detectable as a simulative explosive material using x-ray or electromagnetic mm wave irradiated from a screening device, and
    wherein the amount of glycerol is 29.5% by weight to 45.5% by weight, the amount of acetic acid is 7.625% by weight to 23.625% by weight, and the amount of water is 41.85% by weight to 51.85% by weight.

2. The liquid mixture according to claim 1, wherein the amount of glycerol is about 37.5% by weight, the amount of acetic acid is about 15.625% by weight, and the amount of water is about 46.875% by weight.

3. A liquid mixture for testing and validating screening devices for inspecting objects or persons, the mixture comprising glycerol, acetic acid, and water, wherein the amount of glycerol is about 37.5% by weight, the amount of acetic acid is about 15.625% by weight, and the amount of water is about 46.875% by weight.

4. The liquid mixture according to claim 3, wherein the acetic acid is contained in vinegar essence added in the water.

5. A method for testing and validating screening devices, the method comprising:
- preparing a liquid mixture according to claim 1 the mixture consisting essentially of glycerol, acetic acid and water, the amount of glycerol being 29.5% by weight to 45.5% by weight, the amount of acetic acid being 7.625% by weight to 23.625% by weight, and the amount of water being 41.85% by weight to 51.85% by weight;
- placing the mixture inside an object or on a person;
- inspecting, by the screening devices, the object or person to determine the presence of the mixture, the determination of the presence of the mixture providing validation of the screening devices.

* * * * *